(12) United States Patent
Mehra

(10) Patent No.: US 10,744,175 B2
(45) Date of Patent: Aug. 18, 2020

(54) HERBAL COMPOSITION FOR THE TREATMENT OF HERPES

(71) Applicant: Apurve Mehra, Culver City, CA (US)

(72) Inventor: Apurve Mehra, Culver City, CA (US)

( * ) Notice: Subject to any disclaimer, the term of this patent is extended or adjusted under 35 U.S.C. 154(b) by 439 days.

(21) Appl. No.: 15/438,552

(22) Filed: Feb. 21, 2017

(65) Prior Publication Data

US 2017/0239309 A1 Aug. 24, 2017

Related U.S. Application Data

(60) Provisional application No. 62/298,673, filed on Feb. 23, 2016.

(30) Foreign Application Priority Data

Feb. 23, 2016 (IN) .............................. 201621006257

(51) Int. Cl.

| | | |
|---|---|---|
| A61K 36/324 | (2006.01) | |
| A61K 36/185 | (2006.01) | |
| A61K 36/484 | (2006.01) | |
| A61K 36/48 | (2006.01) | |
| A61K 36/63 | (2006.01) | |
| A61K 31/122 | (2006.01) | |
| A61K 36/738 | (2006.01) | |
| A61K 36/38 | (2006.01) | |
| A61K 9/20 | (2006.01) | |

(52) U.S. Cl.
CPC .......... *A61K 36/324* (2013.01); *A61K 31/122* (2013.01); *A61K 36/185* (2013.01); *A61K 36/38* (2013.01); *A61K 36/48* (2013.01); *A61K 36/484* (2013.01); *A61K 36/63* (2013.01); *A61K 36/738* (2013.01); *A61K 9/205* (2013.01)

(58) Field of Classification Search
None
See application file for complete search history.

(56) References Cited

U.S. PATENT DOCUMENTS

| | | | |
|---|---|---|---|
| 6,284,289 B1 * | 9/2001 | Van den Berghe | .... A61K 36/14 424/746 |
| 8,846,114 B1 * | 9/2014 | Makela | ................ A61K 31/351 424/725 |
| 2017/0266247 A1 * | 9/2017 | Shankar | ................ A61K 36/48 |

FOREIGN PATENT DOCUMENTS

IN        2013 MU00808        *  1/2015

* cited by examiner

*Primary Examiner* — Ralph J Gitomer
(74) *Attorney, Agent, or Firm* — Howard & Howard Attorneys PLLC

(57) ABSTRACT

Disclosed herein is a therapeutic herbal composition comprising extracts of herbs selected from *Hypericum mysorense, Holoptelia integrifolia, Terminalia chebula, Glycyrrhiza glabra, Acacia Catechu, Rosa canina, Tecoma avellanedae, Olea europaea, Boswellia serratta* and optionally comprises Asthaxantin along with pharmaceutical acceptable excipients, useful for the treatment of symptoms associated with Herpes simplex virus, Human papilloma virus and other viral infections. The invention further discloses a method of treating the Herpes simplex virus, Human papilloma virus and other viral infections by administering said therapeutic herbal composition to a subject in need thereof.

14 Claims, No Drawings

HERBAL COMPOSITION FOR THE TREATMENT OF HERPES

CROSS-REFERENCE TO RELATED APPLICATION

This application claims priority to U.S. Provisional Patent Application Ser. No. 62/298,673, filed Feb. 23, 2016 and to Indian Patent Application No. 201621006257, filed Feb. 23, 2016, the disclosures of which are hereby incorporated by reference in their entirety.

TECHNICAL FIELD OF THE INVENTION

The present invention relates to herbal composition for the treatment of Herpes simplex virus, Human papilloma virus and other viral infections. In particular, the present invention relates to a therapeutic composition comprising extracts of herbs *Hypericum mysorense, Holoptelia integrifolia, Terminalia chebula, Astaxanthin, Glycyrrhiza glabra, Acacia Catechu, Rosa canina, Tecoma avellanedae, Olea europaea* and *Boswellia serratta* along with pharmaceutical acceptable excipients. The present invention also relates to the process of preparation of said composition. The invention further relates to a method of treating the Herpes simplex virus, Human papilloma virus and other viral infections by administering the composition of present invention to a subject in need thereof.

BACKGROUND OF THE INVENTION

Herpes is a viral disease from the herpes viridae family caused by both Herpes Simplex Virus type 1 (HSV-1) and Herpes Simplex Virus type 2 (HSV-2). An outbreak of the herpes virus leads to cold sores which can occur on the genitals, mouth and along nerve pathways.

Infection with the herpes virus is categorized into one of several distinct disorders based on the site of infection. Oral herpes, the visible symptoms of which are colloquially called cold sores or fever blisters, is an infection of the face or mouth. Oral herpes is the most common form of infection. Genital herpes, is the second most common form of herpes. Other disorders such as herpetic whitlow, herpes gladiatorum, ocular herpes, cerebral herpes infection encephalitis, Mollaret's meningitis, neonatal herpes, and possibly Bell's palsy are all caused by herpes simplex viruses.

Herpes viruses cycle between periods of active disease presenting as blisters containing infectious virus particles that last 2-21 days, followed by a remission period. Genital herpes, however, is often asymptomatic, though viral shedding may still occur. After initial infection, the viruses are transported along sensory nerves to the sensory nerve cell bodies, where they become latent and reside lifelong. Causes of recurrence are uncertain, though some potential triggers have been identified, including immunosuppressant drugs.

The previously latent virus then multiplies new virus particles in the nerve cell and these are transported along the axon of each neuron to the nerve terminals in the skin, where they are released. Over time, episodes of active disease reduce in frequency and severity.

Herpes simplex is most easily transmitted by direct contact with a lesion or the body fluid of an infected individual. Transmission may also occur through skin-to-skin contact during periods of asymptomatic shedding. Barrier protection methods are the most reliable method of preventing transmission of herpes, but they merely reduce rather than eliminate risk. Oral herpes is easily diagnosed if the patient presents with visible sores or ulcers. Early stages of orofacial herpes and genital herpes are harder to diagnose; laboratory testing is usually required.

Further, the herpes virus resides in the nerve ganglia behind the blood brain barrier in a place where the immune system and antiviral drugs cannot get to it. The opportunistic HSV virus moves from its dormant state to an active herpes outbreak when it finds that the body's immunity is compromised, making it a very difficult virus to cure. Furthermore, these viruses are known to be efficient genetic mutators and have the ability to remain hidden from the immune system for long periods of time. This means that over a period of time, the DNA of the virus changes and they become resistant to antivirals, making herpes difficult to combat with conventional medicine such as Aciclovir (ACV), Penciclovir etc.

In view of the above, the inventors of the present invention felt a need to develop a herbal composition that will combat these difficulties posed by the herpes virus and which will support the immune function within the body making it an inhospitable place for viral infections to proliferate.

SUMMARY OF THE INVENTION

In accordance with the above, in one aspect, the present invention provides a therapeutic herbal composition comprising extracts of herbs selected from *Hypericum mysorense, Holoptelia integrifolia, Terminalia chebula, Glycyrrhiza glabra, Acacia Catechu, Rosa canina, Tecoma avellanedae, Olea europaea* and *Boswellia serratta* along with pharmaceutical acceptable excipients useful in the treatment of Herpes simplex virus, Human papilloma virus and other viral infections.

In another aspect, the present invention provides a therapeutic herbal composition comprising extracts of herbs selected from *Hypericum mysorense, Holoptelia integrifolia, Terminalia chebula, Glycyrrhiza glabra, Acacia Catechu, Rosa canina, Tecoma avellanedae, Olea europaea* and *Boswellia serratta*; wherein said composition optionally comprises Astaxanthin along with pharmaceutical acceptable excipients useful in the treatment of Herpes simplex virus, Human papilloma virus and other viral infections.

In yet another aspect, the present invention provides a process for preparation of said herbal composition(s).

In yet another aspect, the invention provides a method of treating the Herpes simplex virus, Human papilloma virus and other viral infections by administering said therapeutic herbal composition(s) to a subject in need thereof.

DETAILED DESCRIPTION OF THE INVENTION

The invention will now be described in detail in connection with certain preferred and optional embodiments, so that various aspects thereof may be more fully understood and appreciated. However, any skilled person will appreciate the extent to which such embodiments could be extrapolated in practice.

Source of the Plant Material

At least some of the herbs used in the present invention are collected from naturally grown forests of Kudremukh mountain range a peak located in Chikkamagaluru district-Karnataka and others procured from suppliers.

Standardization

All the ingredients of the present composition are well standardized with acceptable impurity profiles. The raw materials as well as the finished product were well evaluated for their heavy metal residues which is the major concern with herbal products. All the ingredients are reported to be safe in literature; further, the product of the present invention has been proven to be safe.

In an embodiment, the present invention discloses a therapeutic herbal composition comprising extract of herbs selected from *Hypericum mysorense, Holoptelia integrifolia, Terminalia chebula, Glycyrrhiza glabra, Acacia Catechu, Rosa canina, Tecoma avellanedae, Olea europaea* and *Boswellia serratta* along with pharmaceutical acceptable excipients, useful in the treatment of symptoms associated with Herpes simplex virus, Human papilloma virus and other viral infections.

A brief description of the herbs used in the present composition is as follows:

| Sr. No. | Scientific Name | Common Name | Part used |
| --- | --- | --- | --- |
| 1. | *Hypericum mysorense* | Basant | Ariel parts |
| 2. | *Holoptelia integrifolia* | Chirabilwa | Bark |
| 3. | *Terminalia chebula* | Haritaki | Fruit |
| 4. | *Glycyrrhiza glabra* | Yasthimadhu/ Liquorice | Roots |
| 5. | *Acacia Catechu* | Khadira | Seeds |
| 6. | *Rosa canina* | Rose hips | Petals and ripe hips |
| 7. | *Tecoma avellanedae* | Pau d'Arco | Inner bark |
| 8. | *Olea europaea* | Olive | Leaf |
| 9. | *Boswellia serratta* | Shallaki | Gum/Oleo resin |

The mode of action of the each ingredient used in the present composition is as follows: The ariel part extract of *Hypericum mysorense* and bark of *Holoptelia integrifolia* have antiviral properties. These antiviral properties have been demonstrated in-vitro. In the body however they need a transport to get past the cell wall. Pipali (*Piper longum*) is transport traditionally used in Ayurveda. However, *Piper longum* heats up the channels in the body to allow for transport of actives and heating the body is not recommended in herpes which thrives on hot conditions. The fruit extract of *Terminalia chebula* serves as the cooling transport that allows for the aforementioned antiviral herb *Hypericum mysorense* and *Holoptelia integrifolia* to have affect on the viral cells.

The root extract from *Glycyrrhiza glabra* has antiulcer, antiviral, antihapatotoxic, alkalizing antifungal and anti-HSV properties.

Further, the leaf extracts of *Olea europaea* relaxes the whole nervous system, it is cerebrovascular stimulating, a circulatory stimulant, and it accelerates wound healing and is known to possess antibacterial, antifungal, antiamoebic and anti-inflammatory activities. *Rosa canina* significantly enhances cellular immunity.

*Tecoma avellanedae* and *Acacia Catechu* have potent antiseptic and anti-inflammatory properties also help in quick healing and antiseptic properties.

*Boswellia serratta* (Oleo-gum resin) contains 5-10% essential oils, 20-30% polysaccharides and 40-60% boswellic acid. The oleo-gum resin from *Bosweliia serratta* has the ability to act as binder that helps in sustained release matrix formation and it also helps in preservation.

In another embodiment, the present invention discloses a therapeutic herbal composition comprising extract of herbs selected from *Hypericum mysorense, Holoptelia integrifolia, Terminalia chebula, Glycyrrhiza glabra, Acacia Catechu, Rosa canina, Tecoma avellanedae, Olea europaea* and *Boswellia serratta* wherein said composition optionally comprises Astaxanthin along with pharmaceutical acceptable excipients useful in the treatment of Herpes simplex virus, Human papilloma virus and other viral infections.

Asthaxantin is an essential and potent antioxidant molecule that can cross the blood brain barrier. Asthaxanthin has the ability to prevent nerve damage and Ganglion cell damage. Further, Asthaxanthin transports the antivirals and make them available in the nerve ganglia where the virus resides. Asthaxantin used in the present invention is in the form of beadlets that may be dry blended into the herbal mix.

Accordingly, in a preferred embodiment, the present invention discloses the herbal composition comprising extracts of herbs selected from,
a) *Hypericum mysorense* of about 500 mg to 600 mg;
b) *Holoptelia integrifolia* of about 25 mg to 35 mg;
c) *Terminalia chebula* of about 35 mg to 45 mg;
d) *Glycyrrhiza glabra* of about 90 mg to 100 mg;
e) *Acacia Catechu* of about 35 mg to 40 mg;
f) *Olea europaea* of about 50 mg to 60 mg;
g) *Rosa canina* of about 50 mg to 60 mg;
h) *Tecoma avellanedae* of about 50 mg to 60 mg; and
i) Oleo resin/Gum of *Boswellia serratta* of about 50 mg to 60 mg of total composition along with pharmaceutical acceptable excipients (q.s).

In another preferred embodiment, the present invention discloses the herbal composition comprising extracts of herbs selected from,
a) *Hypericum mysorense* of about 500 mg;
b) *Holoptelia integrifolia* of about 28 mg;
c) *Terminalia chebula* of about 38 mg;
d) *Glycyrrhiza glabra* of about 95 mg;
e) *Acacia Catechu* of about 38 mg;
f) *Olea europaea* of about 55 mg;
g) *Rosa canina* of about 55 mg;
h) *Tecoma avellanedae* of about 58 mg; and
i) Oleo resin/Gum of *Boswellia serratta* of about 60 mg of total composition along with pharmaceutical acceptable excipients (q.s).

Accordingly, in yet another embodiment, the present invention discloses the herbal composition comprising extracts of herbs selected from,
a) *Hypericum mysorense* of about 500 mg to 600 mg;
b) *Holoptelia integrifolia* of about 25 mg to 35 mg;
c) *Terminalia chebula* of about 35 mg to 45 mg;
d) *Glycyrrhiza glabra* of about 90 mg to 100 mg;
e) *Acacia Catechu* of about 35 mg to 40 mg;
f) *Olea europaea* of about 50 mg to 60 mg;
g) *Rosa canina* of about 50 mg to 60 mg;
h) *Tecoma avellanedae* of about 50 mg to 60 mg;
i) Oleo resin/Gum of *Boswellia serratta* of about 50 mg to 60 mg; and
j) Asthaxantin of about 1 mg to 3 mg of total composition along with pharmaceutical acceptable excipients (q.s).

In yet another preferred embodiment, the present invention discloses the herbal composition comprising extracts of herbs selected from,
a) *Hypericum mysorense* of about 500 mg;
b) *Holoptelia integrifolia* of about 28 mg;
c) *Terminalia chebula* of about 38 mg;
d) *Glycyrrhiza glabra* of about 95 mg;
e) *Acacia Catechu* of about 38 mg;
f) *Olea europaea* of about 55 mg;
g) *Rosa canina* of about 55 mg;
h) *Tecoma avellanedae* of about 58 mg;
i) Oleo resin/Gum of *Boswellia serratta* of about 60 mg to; and
j) Asthaxantin of about 2 mg of total composition along with pharmaceutical acceptable excipients (q.s).

The said herbal extracts are derived from whole plant or aerial parts or different parts of the plant such as root, bark, leaf, fruit, flower buds, oleo resin/gum and the like.

In another preferred embodiment, the present invention provides a process for preparation of composition of the present invention comprises the steps of,
- a) identifying, washing and agitating each herb followed by mixing and digesting together in a rotary extractor to obtain a decoction liquid;
- b) mixing the decoction liquid of step (a) in a continuous rotary motion with strict control of the extraction temperature between 60 to 70° C. for 6 hrs.;
- c) passing the extraction of step (b) into low-temperature vacuum evaporator followed by concentrating to obtain a viscous liquid;
- d) piping the concentrated viscous liquid of step (c) in to the flow coater (granulator) which sprays the concentrate onto minute particles of powdered herbs (base material) and drying them to obtain concentrated granules followed by weighing and pressing to obtain the desired product.

The composition of the present invention is preferably in the form of a table. Accordingly, the process for preparation of tablet composition of the present invention comprises:

1. Extraction:

Each herb included in the composition is properly identified, cleaned, washed, and agitated according to a specific protocol for each herb. After all foreign materials are meticulously removed; the ingredients are mixed and digested together in a rotary extractor. A continuous rotary motion thoroughly mixes the decoction liquid with strict control of the extraction temperature and timing. This unique extractor includes an essential oil retrieval system which allows the vat to capture and preserve the volatile oils, which are reintroduced later in the granulation phase.

2. Evaporation (Concentration):

Once extraction is complete, the content is passed through rotary extractor and the decoction flows directly into a low-temperature vacuum evaporation-concentration system. This low-temperature system eliminates the damaging effects that high temperatures can have on formula potency.

3. Granulation and Tableting:

From the concentration chambers the herbs now in the form of a viscous liquid, are piped into a flow coater in a closed system, there is a 0% chance of cross-contamination as the flow coater (granulator) sprays the concentrate onto minute particles of base material and dries them to create concentrated granules. In the present composition, the base material consists of powdered herbs from the ingredients of the formulas themselves. The granules are later precisely measured and pressed into smooth tablets for easy swallowing.

In another embodiment, the invention provides extraction of individual herbs blended with solvents; wherein the herbs in the composition are extracted individually and mixed in proportion as required.

The solvents selected from polar and non-polar solvents such as water, alcohols, hydro-alcohols n-hexane, petroleum ether, dichloromethane, chloroform, acetone and such like either alone or in combination thereof.

The said composition being of herbal origin is susceptible to biological contamination and deterioration during shelf life. Therefore, to minimize or eliminate interaction of herbs used in the composition and to increase the stability and shelf life of the said herbal composition, suitable pharmaceutical excipients are incorporated into the composition. Such excipients or vehicles are selected from the substances known in the technical state and usually utilized for that purpose comprising of natural beta cyclodextrin, water-soluble cyclodextrin derivatives of commercial interest which include the hydroxypropyl derivatives of β-CD; humectants, such as glycerol; glycols, emulsifiers such as the alcohols C1 to C5, sugar alcohols fatty acid ester such as sorbitan fatty acid monoester, viscosity donors or rheology modifiers such as carbopol, or other polymers such as hypermellose as well as preservatives, such as methylparaben and propylparaben.

The quantity of the ingredients used in the herbal composition of the present invention will vary depending upon the body weight of the patient and the mode of administration and can be of any effective amount to achieve the desired therapeutic effect. The recommended dose is one tablet two times daily after meals.

In yet another embodiment, the composition(s) of the present invention is administered via oral route. The oral administration may be accomplished by ingesting the composition in the form of tablet, capsule, granules, paste, pill, syrup or liquid and other suitable dosage forms, preferably a tablet.

In yet another preferred embodiment, the present invention provides method for prevention and treatment of symptoms associated with Herpes simplex virus, Human papilloma virus, and other viral infections wherein said method comprises administering therapeutically effective amount of the herbal composition(s) of the present invention to the subject. The subject mentioned herein is human.

In another preferred embodiment, the present invention provides a method of treating a subject suffering from symptoms associated with Herpes simplex virus and Human papilloma virus and other viral infections comprising administering to a subject in need thereof an effective amount of composition comprising;
- a) aerial part extract of *Hypericum mysorense* of about 500 mg to 600 mg;
- b) bark extract of *Holoptelia integrifolia* of about 25 mg to 35 mg;
- c) fruit extract of *Terminalia chebula* of about 35 mg to 45 mg;
- d) root extract of *Glycyrrhiza glabra* of about 90 mg to 100 mg;
- e) seed extract of *Acacia Catechu* of about 35 mg to 40 mg;
- f) leaf extract of *Olea europaea* of about 50 mg to 60 mg;
- g) petals and rose hips extract of *Rosa canina* of about 50 mg to 60 mg;
- h) inner bark extract of *Tecoma avellanedae* of about 50 mg to 60 mg; and
- i) oleo resin/Gum of *Boswellia serrata* of about 50 mg to 60 mg of total composition along with pharmaceutical acceptable excipients (q.s);

wherein, the fruit extract of *Terminalia chebula* serves as the cooling transport and allowing the antiviral herb *Hypericum mysorense* and *Holoptelia integrifolia* to have effect on the viral cells; the leaf extracts of *Olea europaea* relaxes the whole nervous system and accelerates wound healing; petals and rose hips extract of *Rosa canina* enhances cellular immunity; inner bark extract of *Tecoma avellanedae* helps in quick healing and Oleo resin/Gum of *Boswellia serratta* helps in binding and preservation.

In yet another preferred embodiment, the present invention provides a method of treating a subject suffering from symptoms associated with Herpes simplex virus and Human papilloma virus and other viral infections comprising administering to a subject in need thereof an effective amount of composition comprising;
- a) aerial part extract of *Hypericum mysorense* of about 500 mg to 600 mg;
- b) bark extract of *Holoptelia integrifolia* of about 25 mg to 35 mg;
- c) fruit extract of *Terminalia chebula* of about 35 mg to 45 mg;
- d) root extract of *Glycyrrhiza glabra* of about 90 mg to 100 mg;
- e) seed extract of *Acacia Catechu* of about 35 mg to 40 mg;
- f) leaf extract of *Olea europaea* of about 50 mg to 60 mg;
- g) petals and rose hips extract of *Rosa canina* of about 50 mg to 60 mg;
- h) inner bark extract of *Tecoma avellanedae* of about 50 mg to 60 mg;
- i) oleo resin/gum of *Boswellia serrata* of about 50 mg to 60 mg; and
- j) Asthaxantin of about 1 mg to 3 mg of total composition along with pharmaceutical acceptable excipients (q.s);

wherein, the fruit extract of *Terminalia chebula* serves as the cooling transport and allowing the antiviral herb *Hypericum mysorense* and *Holoptelia integrifolia* to have effect on the viral cells; the leaf extracts of *Olea europaea* relaxes the whole nervous system and accelerates wound healing; petals and rose hips extract of *Rosa canina* enhances cellular immunity; inner bark extract of *Tecoma avellanedae* helps in quick healing; oleo resin/gum of *Boswellia serratta* helps in binding and preservation and wherein, Asthaxantin transports the antivirals and make them available in the nerve ganglia where the virus resides.

The composition in accordance with the invention can be formulated in the form of tablet, capsule, granules, pill, paste, syrup or liquid. The composition may be preferably administered via oral route.

The method of treating the symptoms associated with Herpes simplex virus and Human papilloma virus includes oral herpes, genital herpes, herpetic whitlow, herpes gladiatorum, ocular herpes, cerebral herpes infection encephalitis, Mollaret's meningitis and neonatal herpes comprises administering an effective amount of the composition(s) of the invention. Further, the other viral infections include warts caused by the Human papilloma virus (HPV) and infection of abnormal cells (pre-cancerous cells) can also be effectively treated by administering the composition(s) of the invention.

In yet another embodiment, the invention provides use of the herbal composition(s) of the present invention in preparing the medicament intended to treat the subjects suffering from symptoms associated with Herpes simplex virus, Human papilloma virus and other viral infections.

The symptoms associated with Herpes simplex virus and Human papilloma virus includes oral herpes, genital herpes, herpetic whitlow, herpes gladiatorum, ocular herpes, cerebral herpes infection encephalitis, Mollaret's meningitis, neonatal herpes and the like. The other viral infections include warts caused by the Human papilloma virus (HPV), infection of abnormal cells (pre-cancerous cells) and the like.

Stability Data

Stability study of the composition is carried out as per ICH guideline at accelerated condition of 400° C./75% RH and real time condition of 300° C./65% RH. The composition is stable for 3 years when used under normal condition and no dangerous reactions are acknowledged when used under normal condition.

Some typical examples illustrating the embodiments of the present invention are provided; however, these are exemplary only and should not be regarded as limiting the elements of the present invention.

EXAMPLE 1

Composition 1

| Sr. No. | Scientific Name | Quantity |
|---|---|---|
| 1. | *Hypericum mysorense* | 500 mg to 600 mg |
| 2. | *Holoptelia integrifolia* | 25 mg to 35 mg |
| 3. | *Terminalia chebula* | 35 mg to 45 mg |
| 4. | *Glycyrrhiza glabra* | 90 mg to 100 mg |
| 5. | *Acacia Catechu* | 35 mg to 40 mg |
| 6. | *Olea europaea* | 50 mg to 60 mg |
| 7. | *Rosa canina* | 50 mg to 60 mg |
| 8. | *Tecoma avellanedae* | 50 mg to 60 mg |
| 9. | *Boswellia serratta* | 50 mg to 60 mg |
| 10. | Pharmaceutical acceptable excipients | Q.S. |
| | Total | 1000 mg |

EXAMPLE 2

Composition 2

| Sr. No. | Scientific Name | Quantity |
|---|---|---|
| 1. | *Hypericum mysorense* | 500 mg to 600 mg |
| 2. | *Holoptelia integrifolia* | 25 mg to 35 mg |
| 3. | *Terminalia chebula* | 35 mg to 45 mg |
| 4. | *Rosa canina* | 50 mg to 60 mg |
| 5. | *Glycyrrhiza glabra* | 90 mg to 100 mg |
| 6. | Pharmaceutical acceptable excipients | Q.S. |
| | Total | 1000 mg |

EXAMPLE 3

Composition 3

| Sr. No. | Scientific Name | Quantity |
|---|---|---|
| 1. | *Hypericum mysorense* | 500 mg to 600 mg |
| 2. | *Holoptelia integrifolia* | 25 mg to 35 mg |
| 3. | *Terminalia chebula* | 35 mg to 45 mg |
| 4. | *Glycyrrhiza glabra* | 90 mg to 100 mg |
| 5. | *Acacia Catechu* | 35 mg to 40 mg |
| 6. | *Olea europaea* | 50 mg to 60 mg |
| 7. | *Rosa canina* | 50 mg to 60 mg |
| 8. | *Tecoma avellanedae* | 50 mg to 60 mg |
| 9. | *Boswellia serratta* | 50 mg to 60 mg |
| 10. | Asthaxantin | 1 mg to 3 mg |
| 11. | Pharmaceutical acceptable excipients | Q.S. |
| | Total | 1000 mg |

EXAMPLE 4

Process for Preparation of Composition a) Identifying, washing and agitating each herb in the composition followed by mixing and digesting together in a rotary extractor to obtain a decoction liquid;
b) mixing the decoction liquid of step (a) in a continuous rotary motion with strict control of the extraction temperature between 60 to 70° C. for 6 hrs.;
c) passing the extraction of step (b) into low-temperature vacuum evaporator followed by concentrating to obtain a viscous liquid; and
d) piping the concentrated viscous liquid of step (c) in to the flow coater (granulator) which sprays the concentrate onto minute particles of powdered herbs (base material) and drying them to obtain concentrated granules, weighing and pressing to obtain the desired product.

EXAMPLE 6

One Embodiment of the Composition of the Present Invention Shows Significant Reduction in the Symptoms of Herpes and HPV in Humans 1. Frequent Genital herpes outbreaks—A 36 year old male from Karnataka, India, suffers from severe blistering, pain and burning around the pubic region and genitals due to one or more strains of the Herpes virus. The composition of the invention as disclosed in Example 1 is administered. Within 3 days, the blisters dry up and the subject reports a significant reduction in, if not elimination of, nerve pain. This male subject daily ingests the composition of Example 1 for approximately 4 months and does not report another outbreak of Herpes for the following year.
2. Tiny pimple-like outbreaks around lips—A 21 year old female—starts experiencing tiny pimples on her lips which later appear like blisters. Blood tests show high titer from HSV 1 antibodies. After taking the composition as disclosed in Example 1, the symptoms disappear in 4 days and do not recur.
3. Family from Chennai—A 40 year old man and 35 year old woman each exhibit symptoms of genital discoloration, burning urine, dry and scaly skin with recurrent blistering and burning around the genitals after sexual intercourse. Each tests positive for HSV 1 and 2. Each has been taking the antiviral acyclovir for years with little success. After daily ingesting the composition of Example 1, and consuming a healthy diet, after 5 days their symptoms completely disappear and do not recur.
4. A 34 year old woman reports the presence of abnormal cells along with the presence of HPV. These cells then develop into "pre-cancerous" cells. This subject daily ingests the composition of Example 1 for 4 months. After 4 months, the testing reveals abnormal cells but no HPV. A continuation of the treatment for another 4 months shows a lack of abnormal cells and HPV.
5. A female subject suffers from HPV infection for 4 years and shows high risk HPV infection (possible cancer threat). After administration of the composition of Example 1 for over 6 months, the results for HPV come back negative.
6. A 46 year old female reports warts on her hands for about 6 years which she removes with laser therapy. This burns the skin and leaves scars. After 12 days of daily ingestion of the composition of Example 1, there is a visible shrinking of the warts. After 2 months of treatment, the warts disappear.
7. A 38 year old female reports an HPV infection for 5 years. Within the first 6 months of daily ingestion of the composition of Example 1, all tests for HPV are negative and no recurrence is shown.
8. A 32 year old male ingests the composition of Example 1 along with an alkaline diet. This subject suffers from larger warts (around 10 in number). After ingestion of the composition of Example 1 and the alkaline diet, the number of warts is reduced to 2, which are also smaller in size. After treatment for 10 additional days, the warts no longer appear.

What is claimed is:

1. A therapeutic herbal composition for treatment of symptoms associated with Herpes simplex virus, Human papilloma virus, wherein said composition comprises:
   a) extract of *Hypericum mysorense* of about 500 mg to 600 mg,
   b) extract of *Holoptelia integrifolia* of about 25 mg to 35 mg,
   c) extract of *Terminalia chebula* of about 35 mg to 45 mg,
   d) extract of *Glycyrrhiza glabra* of about 90 mg to 100 mg,
   e) extract of *Acacia Catechu* of about 35 mg to 40 mg,
   f) extract of *Rosa canina* of about 50 mg to 60 mg,
   g) extract of *Tecoma avellanedae* of about 50 mg to 60 mg,
   h) extract of *Olea europaea* of about 50 mg to 60 mg, and
   i) oleo resin/gum of *Boswellia serrata* of about 50 mg to 60 mg, and the composition further comprising pharmaceutical acceptable excipients (q.s.).

2. The composition according to claim 1, wherein
   the extract of *Hypericum mysorense* is about 500 mg,
   the extract of *Holoptelia integrifolia* is about 28 mg,
   the extract of *Terminalia chebula* is about 38 mg,
   the extract of *Glycyrrhiza glabra* is about 95 mg,
   the extract of *Acacia Catechu* is about 38 mg,
   the extract of *Olea europaea* is about 55 mg,
   the extract of *Rosa canina* is about 55 mg,
   the extract of *Tecoma avellanedae* is about 58 mg,
   the oleo resin/gum of *Boswellia serrata* is about 60 mg,
   and the composition further comprising pharmaceutical acceptable excipients (q.s).

3. The composition according to claim 1, wherein said composition further comprises Astaxanthin.

4. The composition according to claim 3, wherein the Astaxanthin is about 1 mg to 3 mg.

5. The composition according to claim 1, wherein said composition is in the form of a tablet, capsule, granules, pill, paste, syrup or liquid.

6. The composition according to claim 1, wherein viral infections associated with herpes simplex virus or human papilloma virus are selected from the group consisting of oral herpes, genital herpes, herpetic whitlow, herpes gladiatorum, ocular herpes, cerebral herpes infection, encephalitis, Mollaret's meningitis and neonatal herpes.

7. The composition according to claim 1, wherein viral infections associated with herpes simplex virus or human papilloma virus are warts caused by the Human papilloma virus (HPV).

8. A method of treating a subject suffering from symptoms associated with Herpes simplex virus or Human papilloma virus, comprising administering to the subject an effective amount of composition comprising;

a) aerial part extract of *Hypericum mysorense* of about 500 mg to 600 mg;
b) bark extract of *Holoptelia integrifolia* of about 25 mg to 35 mg;
c) fruit extract of *Terminalia chebula* of about 35 mg to 45 mg;
d) root extract of *Glycyrrhiza glabra* of about 90 mg to 100 mg;
e) seed extract of *Acacia Catechu* of about 35 mg to 40 mg;
f) leaf extract of *Olea europaea* of about 50 mg to 60 mg;
g) petals and rose hips extract of *Rosa canina* of about 50 mg to 60 mg;
h) inner bark extract of *Tecoma avellanedae* of about 50 mg to 60 mg; and
i) oleo resin/gum of *Boswellia serratta* of about 50 mg to 60 mg, and the composition further comprising pharmaceutical acceptable excipients (q.s);
wherein, the fruit extract of *Terminalia chebula* is a cooling transport and allows the antiviral herb *Hypericum mysorense* and *Holoptelia integrifolia* to have effect on the viral cells; the leaf extracts of *Olea europaea* relaxes the whole nervous system and accelerates wound healing; petals and ripe hips extract of *Rosa canina* enhances cellular immunity; inner bark extract of *Tecoma avellanedae* helps in quick healing and Oleo resin/gum of *Boswellia serratta* helps in binding and preservation.

9. A method of treating a subject suffering from symptoms associated with Herpes simplex virus and Human papilloma virus comprising administering to a subject in need thereof an effective amount of composition comprising;
a) aerial part extract of *Hypericum mysorense* of about 500 mg to 600 mg;
b) bark extract of *Holoptelia integrifolia* of about 25 mg to 35 mg;
c) fruit extract of *Terminalia chebula* of about 35 mg to 45 mg;
d) root extract of *Glycyrrhiza glabra* of about 90 mg to 100 mg;
e) seed extract of *Acacia Catechu* of about 35 mg to 40 mg;
f) leaf extract of *Olea europaea* of about 50 mg to 60 mg;
g) petals and rose hips extract of *Rosa canina* of about 50 mg to 60 mg;
h) inner bark extract of *Tecoma avellanedae* of about 50 mg to 60 mg;
i) oleo resin/gum of *Boswellia serratta* of about 50 mg to 60 mg and
j) Astaxanthin of about 1 mg to 3 mg, and the composition further comprising pharmaceutical acceptable excipients (q.$);
wherein, the fruit extract of *Terminalia chebula* is a cooling transport and allowing the antiviral herb *Hypericum mysorense* and *Holoptelia integrifolia* to have effect on the viral cells; the leaf extracts of *Olea europaea* relaxes the whole nervous system and accelerates wound healing; petals and ripe hips extract of *Rosa canina* enhances cellular immunity; inner bark extract of *Tecoma avellanedae* helps in quick healing; oleo resin/gum of *Boswellia serratta* helps in binding and preservation; and
wherein, Astaxanthin transports the antivirals and make them available in the nerve ganglia where the virus resides.

10. The method according to claim 8, wherein said composition is administered orally.

11. The method according to claim 8, wherein said composition is in the form of tablet, capsule, granules, pill, paste, syrup or liquid.

12. The method according to claim 8, wherein viral infections associated with herpes simplex virus or human papilloma virus are selected from the group consisting of oral herpes, genital herpes, herpetic whitlow, herpes gladiatorum, ocular herpes, cerebral herpes infection, encephalitis, Mollaret's meningitis and neonatal herpes.

13. The method according to claim 8, wherein viral infections associated with herpes simplex virus or human papilloma virus are the Human papilloma virus (HPV).

14. The method according to claim 8, wherein the subject is human.

* * * * *